United States Patent [19]

Felfoldi

[11] 4,192,311

[45] Mar. 11, 1980

[54] DISPOSABLE DIAPER WITH WETNESS INDICATOR

[76] Inventor: James J. Felfoldi, 1919 Frankfort St., San Diego, Calif. 92110

[21] Appl. No.: 857,672

[22] Filed: Dec. 5, 1977

[51] Int. Cl.² .................... A61F 13/16; A61F 13/00
[52] U.S. Cl. .................................... 128/287; 128/296
[58] Field of Search ............... 128/287, 296, 284, 288, 128/290 R

[56] References Cited

U.S. PATENT DOCUMENTS

| | | | |
|---|---|---|---|
| 2,371,390 | 3/1945 | Grave | 128/156 |
| 2,536,631 | 1/1951 | Ely | 128/290 R |
| 3,199,095 | 8/1965 | Ashida | 128/287 |
| 3,675,654 | 7/1972 | Baker et al. | 128/287 |
| 3,759,261 | 9/1973 | Wang | 128/287 |
| 3,794,024 | 2/1974 | Kokx | 128/285 |
| 3,918,454 | 11/1975 | Korodi et al. | 128/287 |
| 3,952,746 | 4/1976 | Summers | 128/287 |
| 4,022,211 | 5/1977 | Timmons et al. | 128/287 |

FOREIGN PATENT DOCUMENTS 977661 of 1975 Canada .................................... 128/284

Primary Examiner—Robert W. Michell
Assistant Examiner—C. W. Shedd
Attorney, Agent, or Firm—William W. Haefliger

[57] ABSTRACT

A disposable article comprises a translucent sheet of substantially water impervious material and a moisture absorbent pad associated with the sheet. Also, a visual indicator is located proximate the sheet, and a mask is located between the indicator and sheet, the mask characterized when dry as masking the visibility of the indicator through the sheet, and further characterized when wet as unmasking the visibility of the indicator.

7 Claims, 5 Drawing Figures

DISPOSABLE DIAPER WITH WETNESS INDICATOR

BACKGROUND OF THE INVENTION

This invention relates generally to disposable articles such as diapers, bandages and sanitary napkins, and more particularly concerns moisture indication or indicators associated with such articles.

Wetness or moisture indicators are disclosed in the following U.S. Patents: U.S. Pat. No. 3,675,654 to Baker discloses a moisture-actuated indicating agent in particulate form; U.S. Pat. No. 2,681,032 to Shaw discloses a low wet-strength element which breaks and a colored indicator moves into registry with an aperture; U.S. Pat. No. 2,254,609 to Kinzer discloses a dye which dissolves in moisture to reveal a color indication; U.S. Pat. No. 2,214,354 discloses use of a deliquescent material which absorbs water, and a dye is then transported through porous material; and U.S. Pat. No. 2,156,880 discloses a dye which changes color in clothing when contacted by perspiration.

None of the above prior art teaches or suggests the novel and unusual moisture indicator of the present invention, which is extremely simple, inexpensive and readily incorporated in a disposable article such as a diaper.

SUMMARY OF THE INVENTION

Basically, the invention is adapted to be incorporated in a disposable articles that comprises a translucent sheet of substantially water impervious material and a moisture absorbent pad closely associated with the sheet, and includes:

(a) a visual indicator proximate said sheet, and (b) a mask between said indicator and said translucent sheet, said mask characterized when dry as masking the visibility of said indicator through the sheet, and further characterized when wet as unmasking said visibility.

As will appear, the mask and indicator are typically disposed between the sheet and a local portion of the pad; the mask may advantageously consist of paper which may be embossed for purposes as will appear; the mask is characterized as becoming translucent when wet; the indicator may advantageously consist of a coloring agent together with material which becomes stained by the agent when wet; the agent is advantageously located between the mask and stainable material; the indicator may alternatively comprise a coloring agent located adjacent the mask and at the side of the latter opposite the transulcent sheet of water impervious material; and the embossed sheet may be folded to retain the indicator spaced from the translucent sheet until the embossed sheet folds collapse when wetted.

Benefits of the invention include:

1. Proper use reduces a baby's exposure to waste elements (urine and/or feces) that cause diaper rash;

2. Proper use helps parents in toilet training;

3. Proper use reduces skin rash due to reduced exposure of baby's skin to bacteria and/or fungus found in feces or urine;

4. Proper use reduces skin rash or any dermatological condition due to acid found in urine;

5. Does not require tapes to be detached to inspect inside the diaper for urine and/or feces;

6. Prolongs life of tape used to keep diaper on;

7. Allows mother to inspect diapers from distance without actually opening diaper;

8. Does not require apertures or slits in plastic film, which could leak fluid.

These and other objects and advantages of the invention, as well as the details of illustrative embodiments, will be more fully understood from the following description and drawings, in which:

DRAWING DESCRIPTION

DETAILED DESCRIPTION

Figure 1:
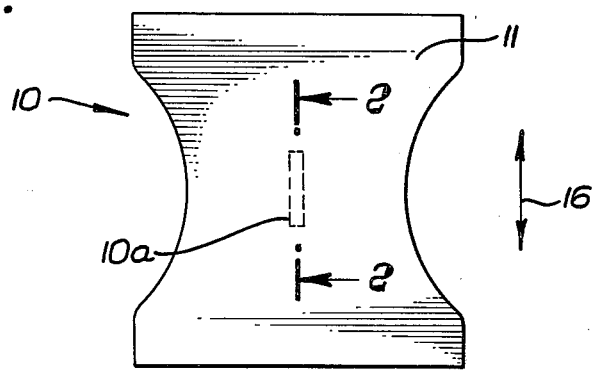
FIG. 1 is a plan view of a diaper incorporating the invention.
Figure 2:
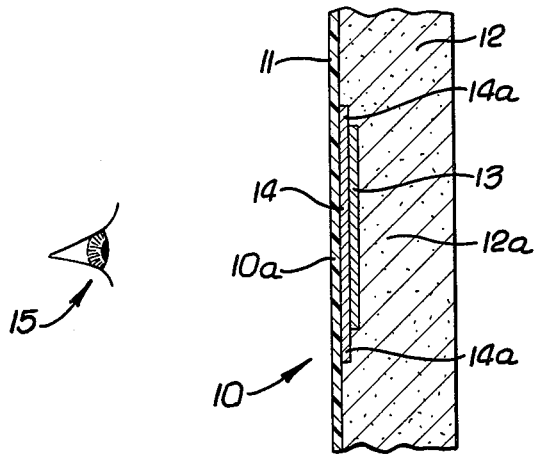
FIG. 2 is an enlarged sectional view taken in lines 2—2 of FIG. 1.

Referring first to FIG. 1, a diaper 10 is shown and may be of disposable type, although other types of diapers are contemplated. In addition, diaper 10 may be considered as representative of other similar articles, such as bandages, training pants, and sanitary napkins, for example. As also shown in FIG. 2, it includes, at the crotch area 10a, a translucent sheet 11 which may consist of suitable plastic film and which is moisture impervious, for protection purposes. That sheet normally is located at the outer side of the diaper, that is at the outer side of moisture pervious pad 12 which is adapted to contact the infant's skin. Pad 12 is considerably thicker than sheet 11.

In accordance with the invention, a visual indicator, as for example at 13, is located proximate the sheet 11, i.e. at its inner side, and a mask 14 is located between the indicator and sheet. The mask is characterized when dry, as masking the visibility of the indicator through the sheet, i.e. as seen from eye position 15; however, when wet, the mask is characterized as unmasking the visibility of the indicator. Both the indicator and mask are located between the local sheet portion 10a and a local portion 12a of the pad 12.

The mask and indicator may extend in superposed, thin strip form, i.e. their combined thickness is less than about 3/16 inch; further, they are typically elongated in the diaper length direction 16.

The mask 14 may be suitably bonded or attached at one side to indicator 13, and at the opposite mask side to the inner side of sheet 11. Also, the sheet 11 may be peripherally attached to the pad, and the sheet and pad may be suitably bonded after positioning of the indicator and pad. Other means of locating the indicator and mask between the sheet and pad may be employed, during fabrication of the diaper. The simplicity of the indicator and mask makes such assembly extremely easy and rapid. Also, no slits or apertures in sheet 11 are required. Such apertures could leak fluid to bed sheets, etc.

Figure 3:
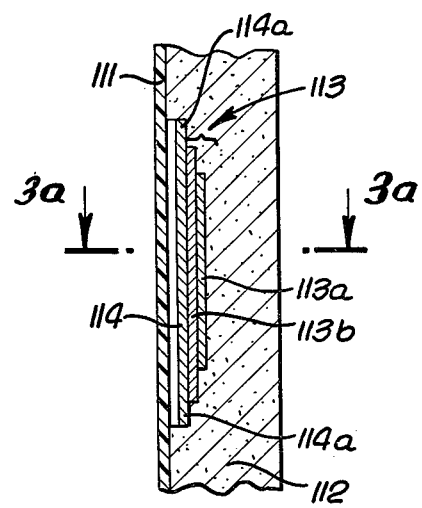
FIG. 3 is a view like FIG. 2, but showing an alternative form.
Figure 3A:
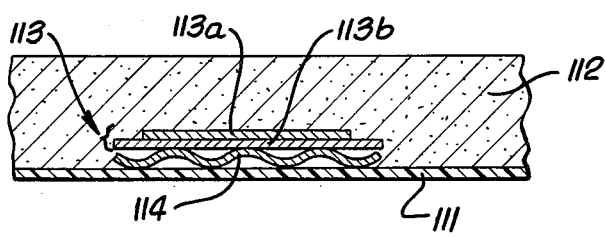
FIG. 3a is a section on lines 3a—3a of FIG. 3.

The mask may consist of paper, which may be embossed so as to be irregular, FIG. 3a showing modified paper mask 114 in corrugated shape, for this purpose. Further, the mask is typically characterized as becoming translucent when wet, as does paper toweling.

In FIG. 2, the indicator consists of or comprises a colored strip such as colored paper. Accordingly, when the mask 14 becomes wet and translucent, the normally invisible colored strip 13 will become visible through translucent or transparent sheet 11, and translucent or transparent strip 14. The latter may be longer or wider than indicator strip 13, to provide moisture absorbing side or end extent at 14a via which moisture is "wicked" or drawn by capillary attraction into the main extent of the mask underlying the indicator.

In FIGS. 3 and 3a, the composite includes embossed mask 114, and indicator 113. The latter includes backer strip 113a which may be colored or uncolored, and a coloring agent such as a layer of ink or dye 113b which tends to "bleed" into, or stain the indicator strip 113a when wet, heightening the visibility of the latter. The folds or corrugations of the embossed mask strip 114 retain the indicator 113 spaced from the translucent sheet 111 until they collapse upon wetting, allowing the indicator to move closer to the sheet 111 to heighten visibility.

Figure 4:
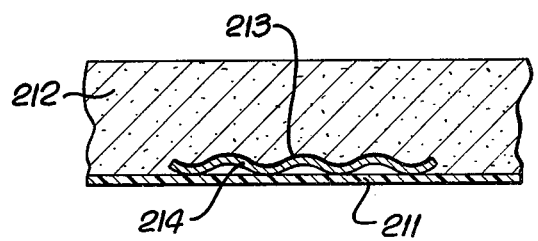
FIG. 4 is a view like FIG. 3a, but showing another modification.

In FIG. 4 the indicator 213 comprises or consists of a coloring agent, such as ink or dye, located adjacent or adherent to the back side of the embossed mask 214, i.e. at the side of the latter opposite sheet 211. When the embossed mask becomes wet, it folds or corrugations relax, allowing movement of the indicator 213 closer to sheet 211, for heightened visibility.

Suitable inks or dyes include those disclosed in U.S. Pat. No. 3,675,654 to Baker.

I claim:

1. In a disposable article comprising a translucent sheet of substantially water impervious material and a moisture absorbent pad closely associated with the sheet, the combination comprising
   (a) a visual indicator proximate said sheet, and
   (b) a mask between said indicator and said sheet, said mask characterized when dry as masking the visibility of said indicator through the sheet, and further characterized when wet as unmasking said visibility by becoming translucent,
   (c) said indicator comprising a coloring agent together with material which becomes stained by the agent when wet, the agent located between the mask and said material, the mask periphery extending a substantial distance into the pad free of the indicator to wick moisture into the mask and thereby expose the indicator,
   (d) the mask being corrugated to define moisture receiving open space between the sheet and indicator,
   (e) said corrugations retain the indicator spaced from the translucent sheet until the corrugations collapse when wet.

2. The combination of claim 1 wherein said mask and indicator are disposed between the sheet and a local portion of the pad.

3. The combination of claim 1 wherein the mask consists of paper.

4. The combination of claim 1 wherein said indicator comprises a coloring agent located adjacent the mask and at the side thereof opposite said translucent sheet.

5. The combination of claim 4 wherein the coloring agent is selected from the group consisting of ink and dye.

6. The combination of claim 1 wherein the indicator consists of a colored strip.

7. The combination of claim 1 wherein the indicator consists of colored paper.

* * * * *